United States Patent [19]

Gautier et al.

[11] Patent Number: 5,214,175
[45] Date of Patent: May 25, 1993

[54] PROCESS FOR THE SYNTHESIS OF MONOHALOALKYLFERROCENES AND 4-CHLOROBUTYLFERROCENE

[75] Inventors: Jean-Claude Gautier, Ablon sur Seine; Jean-Guy Melin, Bolbec; Jean-Claude Mondet, Vert le Grand, all of France

[73] Assignee: Societe Nationale des Poudres et Explosifs, Paris, France

[21] Appl. No.: 766,082

[22] Filed: Sep. 27, 1991

[30] Foreign Application Priority Data

Sep. 27, 1990 [FR] France .................. 90 11913

[51] Int. Cl.$^5$ .............................. C07F 15/02
[52] U.S. Cl. .................. 556/144; 556/143; 556/145
[58] Field of Search .............. 556/143, 145, 144

[56] References Cited

U.S. PATENT DOCUMENTS 3,341,495  9/1967  Neuse .................. 556/143 X
3,420,865  1/1969  Suh et al. .............. 556/143 X

FOREIGN PATENT DOCUMENTS 0362672  4/1990  European Pat. Off. .

OTHER PUBLICATIONS

European Search Report-EP 91 40 2473, May, 1991.
French Search Report-90 11913, May, 1991.
Chemical Abstracts, vol. 81, No. 3, 1974, p. 344, Abstract No. 13631d, Elecko et al: "Synthesis, proton magnetic resonance spectra, and biological activity of haloacylferrocenes".
Chemical Abstracts, vol. 113, No. 12, 1990, p. 146, Abstract No. 99893e, Sakaeda et al: "Ferrocene derivatives for surfactants for manufacature of thin organic films".
Chemical Abstracts, vol. 113, 1990, p. 521, Abstract No. 180081k, Shu et al: "A heterobinuclear cation containing two electroactive centers that 'diffuse' through Nafion coating by difference mechanisms", 1990.
Chemical Abstracts, vol. 80, No. 3, 1974, p. 443, Abstract No. 15044t, Kazakova et al: "Ionic hydrogenation of acetylferrocenes".
Chemical Abstracts, vol. 114, No. 17, 1991, p. 807, Abstract No. 164514u, Sakaeda et al: "Preparation of ferrocenes with metal catalysts".
Chemical Abstracts, vol. 91, No. 5, 1979, p. 558, Abstract No. 38574g, Kolomnikova et al: "Ionic hydrogenation of olefins on heterogeneous catalysts".

Primary Examiner—Arthur C. Prescott
Attorney, Agent, or Firm—Cushman, Darby & Cushman

[57] ABSTRACT

The present invention relates to a process for the synthesis of a monohaloalkylferrocene by reaction of hydrogen with a monohaloalkanoylferrocene in the presence of $PtO_2$ and $SnCl_2$ as catalyst in an acetic acid medium.

In this manner, a crude, particularly pure synthetic product is obtained in a high yield, simply and inexpensively.

The monohaloalkylferrocenes are especially useful as surfactants or as intermediates for the synthesis of combustion catalysts for propergols.

The present invention also relates to a novel monohaloalkylferrocene, namely 4-chlorobutylferrocene.

11 Claims, No Drawings

PROCESS FOR THE SYNTHESIS OF MONOHALOALKYLFERROCENES AND 4-CHLOROBUTYLFERROCENE

The present invention relates to a novel process for the synthesis of monohaloalkylferrocenes and to a novel monohaloalkylferrocene, namely 4-chlorobutylferrocene.

Monohaloalkylferrocenes are especially useful as surfactants or as intermediates for the synthesis of ferrocene-containing combustion catalysts for propellants such as the silylferrocene compounds described in French Patent 2,567,890 or the ethylenically unsaturated polymers comprising silylferrocene groups described in French Patent 2,567,895, via magnesium, followed by reaction with a dialkylhalosilane.

European Patent 331,745 describes monohaloalkylferrocenes whose alkyl chain comprises between 11 and 18 carbon atoms. These compounds, which are used as surfactants or intermediates for the synthesis of surfactants, are obtained by chemical reduction (Zn—mercuric chloride) of the corresponding monohaloalkanoylferrocenes in concentrated ethanol-HCl medium. The crude product obtained is purified by chromatography on a silica column. The yield is not very high, about 75%, and this process has the twin disadvantage of requiring large amounts of toxic mercuric salt and of comprising a purification step of the crude synthetic product.

Moreover, it is in general very problematical to carry out chemical reductions of ketones to hydrocarbons on an industrial scale.

Rosenblum and Wodward, J.A.C.S., 1958, 80, 5443-5449, describe the catalytic reduction of monoacetylferrocene to monoethylferrocene at 20° C. in an acetic acid medium and in the presence of $PtO_2$ catalyst (15 g per mole of ferrocene derivative). The hydrogenation time of 70 hours and the abovementioned amount of the very expensive catalyst prohibit its use, especially on an industrial scale. The yield of 77% is not very high. Moreover, the crude product obtained is very impure and has to be subjected to two purification treatments by column chromatography on alumina followed by distillation.

As far as the Applicant knows, no process for the catalytic hydrogenation of monohaloalkanoylferrocenes to give the corresponding monohaloalkylferrocenes is known, the greatest difficulty consisting in reducing the carbonyl group without reducing the halide.

Mitchell and Yee-Hing Lai note, for example, in Tetrahedron Letters, Vol. 21, 1980, pages 2637-2638, that

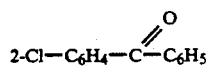

is reduced to $C_6H_5$—$CH_2$—$C_6H_5$ by catalytic hydrogenation in the presence of Raney nickel as catalyst, which means that the carbonyl group and the halide are both reduced. Moreover, the presence of halogen can likewise lead to undesirable side reactions, such as formation of the corresponding hydroxy derivative, followed by formation of the acetoxy derivative if the reaction is carried out in an acetic acid medium.

Persons skilled in the art are therefore trying to find a process for the catalytic reduction of monohaloalkanoylferrocenes to the corresponding monohaloalkylferrocenes which gives very high yields, is simple and inexpensive to carry out on an industrial scale, makes it possible to obtain a crude synthetic product of very high purity insofar as it is very difficult and expensive to purify the crude synthetic monohaloalkylferrocenes obtained after filtration of the catalyst and evaporation of the solvent, especially those whose alkyl chain comprises a large number of carbon atoms, shows the best possible compromise between the amount of catalyst to be used, which to a large extent determines the cost of hydrogenation, and the time needed for the reaction, which determines the productivity. In this respect, it does not seem reasonable that the reaction time exceeds about 12 hours and that the amount of noble catalyst exceeds 2 g per mole of the product to be reduced.

The object of the present invention is to propose such a process.

Unexpectedly, the Applicant has found that the use of a $PtO_2$—$SnCl_2$ mixture as catalyst in an acetic acid medium makes it possible to carry out the catalytic hydrogenation of the monohaloalkanoylferrocenes to the corresponding monohaloalkylferrocenes in a simple and inexpensive manner and in a very high yield, which is in general above or close to 90%, without any substantial reduction of the halide, within a very reasonable time of 10 to 12 hours, using a small quantity of $PtO_2$, about 1.4 g of Pt per mole of ferrocene derivative to be reduced, while, at the same time, a crude synthetic product is obtained whose purity is in general close to 95% and which does not require, in particular, subsequent purification for its use as intermediate for the synthesis of ferrocene-containing combustion catalysts for propellants.

The process for the synthesis of a monohaloalkylferrocene by reduction of a monohaloalkanoylferrocene is characterised according to the invention in that hydrogen is reacted with a monohaloalkanoylferrocene in the presence of a mixture of $PtO_2$ and $SnCl_2$ as catalyst in acetic acid. Preferably, the monohaloalkanoylferrocene has the general formula (I)

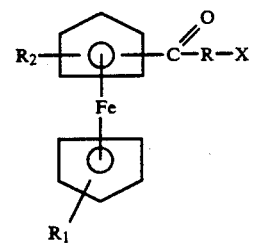

in which $R_1$ and $R_2$ which are identical or different, represent hydrogen or an alkyl chain comprising 1 to 8 carbon atoms, preferably hydrogen, X represents chlorine or bromine, R represents an alkyl chain comprising 2 to 47 carbon atoms, preferably between 2 and 17 carbon atoms, and particularly preferably between 2 and 7 carbon atoms, including limits.

Accordingly, a monohaloalkylferrocene is obtained which has the general formula (II)

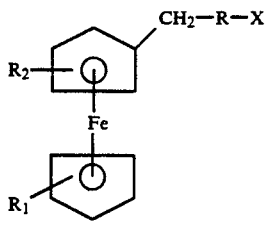

in which $R_1$, $R_2$, R and X have the meaning given above.

According to a preferred variant, R represents a polymethylene group $(CH_2)_n$ in which n is an integer such that $2 \leq n \leq 7$; n is preferably 3.

According to the invention, the catalyst is a mixture of $PtO_2$ and $SnCl_2$. Preferably, between 3 and 7% by weight of $SnCl_2$, relative to the weight of platinum of the $PtO_2$ used is used. Particularly preferably, this percentage is between 3.2 and 4.5%.

As for the $PtO_2$, it is possible to use amounts as low as 0.2% by weight, relative to the monohaloalkanoylferrocene expressed as weight of platinum relative to the weight of monohaloalkanoylferrocene. Preferably, the platinum of $PtO_2$ represents between 0.2 and 2% by weight, relative to the monohaloalkanoylferrocene and particularly preferably, between 0.2 and 0.6% by weight. In this manner, an excellent compromise between reaction time and amount of catalyst is obtained. It is of course also possible to use larger amounts than 2% by weight, but the compromise is then less favourable despite a shorter reaction time.

The reaction temperature is preferably between 15° C. and 45° C., for example ambient temperature, 20° to 25° C. Above 45° C., side reactions take place, especially a reduction of the halide to the corresponding alcohol and acetate, this reduction being all the more pronounced the higher the temperature.

The hydrogen pressure is in general between 100 and 3000 KPa. Elevated pressure is favourable to the reaction kinetics but requires more complex equipment and procedure. A pressure around 500 KPa represents a good compromise.

Since the hydrogenation reaction takes place in a heterogenous medium, it is necessary to stir the reaction medium.

The concentration of the monohaloalkanoylferrocene in the acetic acid is in general between 0.1M and 1M.

The non-limiting examples which follow illustrate the invention and the advantages it provides.

EXAMPLES 1 TO 11

Synthesis of 4-chlorobutylferrocene by hydrogenation of 4-chlorobutyroylferrocene Example 1 was carried out in a 500 cm³ high-pressure stainless steel reactor equipped with a double jacket connected to heat-regulated oil circulation. The reaction mixture is present in a glass beaker placed in the reactor, in order to avoid any contact between this mixture and the stainless steel wall of the reactor. A temperature sensor and a hydrogen pressure gauge are connected to the reactor. Stirring is ensured by means of a magnetic stirrer placed on the reactor, a magnetic stirring bar being placed on the bottom of the glass beaker.

In an inert atmosphere, 170 mg of $PtO_2.xH_2O$ (containing 80% of Pt) and 5 mg of anhydrous $SnCl_2$ are introduced into the glass beaker. 120 cm³ of glacial acetic acid and 29.1 g (0.10 mol) of 4-chlorobutyroylferrocene whose main impurities are 1.4% by weight of ferrocene and 0.88% by weight of 1,1'-di(4-chlorobutyroyl)ferrocene are then poured in. This 4-chlorobutyroylferrocene was obtained in the customary manner by a reaction of the Friedel-Crafts type between ferrocene and 4-chlorobutyryl chloride in $CH_2Cl_2$ in the presence of $AlCl_3$ as catalyst, followed by recrystallisation of the crude product obtained from hexane.

After sealing the reactor and adjusting the temperature to 25° C., it is evacuated and flushed with argon 5 times, and then evacuated and flushed with hydrogen 5 times. The hydrogen pressure is then brought to 500 KPa, and magnetic stirring is then started. The consumption of hydrogen is monitored by means of the pressure gauge. The reactor is recharged with hydrogen during the course of the operation as soon as the pressure falls below 350 KPa.

The reaction is complete after 12 hours.

The reaction medium is then filtered under vacuum, the filtrate is then evaporated in a rotary evaporator, in order to remove the maximum amount of acetic acid. 200 cm³ of $CH_2Cl_2$ are then added, and the organic phase is neutralised by means of 100 cm³ of an aqueous solution containing 4% of $Na_2CO_3$.

After decanting, the organic phase is separated and washed with water until neutral and then dried over magnesium sulphate.

After filtration to remove the magnesium sulphate, and evaporation of the solvent, 26.65 g of crude 4-chlorobutylferrocene (yield 92.5%), which is identified by ¹H NMR and IR spectroscopy as well as by elemental analysis, are obtained. The iron content is 20.4% (theory 20.3%) and the chlorine content is 12.2% (theory 12.8%). Analysis by gas-phase chromatography shows that this crude product contains 1.47% of ferrocene and 0.74% of 1,1'-di(4-chlorobutyl)ferrocene. Analysis by thin layer chromatography (TLC) shows that it also contains 1.45% of 4-hydroxybutylferrocene. Moreover, its water content is 0.042% (K. Fischer method). The purity of this crude product is of the order of 96%.

Examples 2 to 11 were carried out by the same general procedure as that of Example 1, but in a smaller (125 cm³) similarly equipped reactor.

For Examples 2 to 8, 2.91 g (0.01 mol) of 4-chlorobutyroylferrocene, 30 cm³ of acetic acid and 36.4 mg of $PtO_2.xH_2O$ (containing 80% of Pt), which corresponds to 1% by weight of platinum, relative to 4-chlorobutyrylferrocene, were used. The temperature is 25° C. and the hydrogen pressure is between 400 and 500 KPa. These Examples 2 to 8 only differ by the amount of $SnCl_2$ used. Table 1 below lists for each of these examples the amount of $SnCl_2$ used, expressed in % by weight, relative to the amount of platinum employed, and the time of the corresponding half reaction.

TABLE 1

| Ex No. | $SnCl_2$ (%) | Half-reaction time (min) |
|---|---|---|
| 2 | 2.35 | 44 |
| 3 | 2.90 | 36 |
| 4 | 3.40 | 29 |
| 5 | 4.05 | 30 |
| 6 | 5.20 | 38 |

TABLE 1-continued

| Ex No. | SnCl$_2$ (%) | Half-reaction time (min) |
|---|---|---|
| 7 | 6.70 | 36 |
| 8 | 10.00 | 51 |

It can be seen that unexpectedly the amount of SnCl$_2$ passes through an optimum value around 3.7% by weight relative to the Pt of PtO$_2$.

For Examples 9 to 11, 2.91 g (0.01 mol) of 4-chlorobutyroylferrocene, 30 cm$^3$ of acetic acid and 10% by weight of SnCl$_2$, relative to the amount of platinum employed, which is different in the 3 experiments, were used. The temperature is 25° C. and the hydrogen pressure between 400 and 500 KPa. Table 2 below lists for each of these examples the amount of platinum used in the form of PtO$_2$.xH$_2$O (containing 80% of Pt) expressed in weight of Pt relative to 4-chlorobutyrylferrocene, the reaction time and the yield of 4-chlorobutylferrocene obtained.

TABLE 2

| Ex No. | Pt (%) | Time (h) | Yield (%) |
|---|---|---|---|
| 9 | 3.7 | 2.5 | 92.5 |
| 10 | 1.0 | 4.0 | 95.0 |
| 11 | 0.5 | 10.0 | 93.5 |

We claim:

1. A process for the synthesis of a monohaloalkylferrocene by reduction of a monohaloalkanoylferrocene comprising reacting said monohaloalkanoylferrocene with hydrogen in the presence of a mixture of PtO$_2$ and SnCl$_2$ as catalyst in acetic acid.

2. The process of claim 1 wherein said monohaloalkanoylferrocene has formula (I)

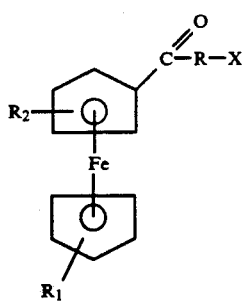

wherein
R$_1$ and R$_2$, each independently, represent hydrogen, or alkyl having 1-8 carbon atoms,
X represents chlorine or bromine
R represents alkyl having 2-47 carbon atoms, and said monohaloalkylferrocene has formula (II)

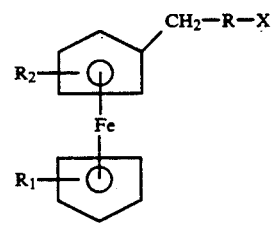

wherein, R$_1$, R$_2$, X and R have the meanings given above.

3. The process of claim 2 wherein R is (CH$_2$)$_n$ wherein n is an integer such that $2 \leq n \leq 7$.

4. The process of claim 3 wherein n is 3.

5. The process of claim 2 wherein R$_1$ and R$_2$ represent hydrogen.

6. The process of claim 1 wherein said SnCl$_2$ is present in an amount ranging from 3 to 7 percent by weight relative to the weight of Pt of said PtO$_2$.

7. The process of claim 1 wherein said SnCl$_2$ is present in an amount ranging from 3.2 to 4.5 percent by weight relative to the weight of Pt of said PtO$_2$.

8. The process of claim 1 wherein the amount of PtO$_2$, expressed in weight of platinum, ranges from 0.2 to 2 percent of the weight of said monohaloalkanoylferrocene.

9. The process of claim 1 wherein the amount of PtO$_2$, expressed in weight of platinum, ranges from 0.2 to 0.6 percent of the weight of said monohaloalkanoylferrocene.

10. The process of claim 1 wherein the reaction temperature ranges from 15° C. to 45° C.

11. The process of claim 10 wherein the concentration of said monohaloalkanoylferrocene in said acetic acid ranges from 0.1M to 1M.

* * * * *